US006960921B2

(12) United States Patent
Kaiser et al.

(10) Patent No.: US 6,960,921 B2
(45) Date of Patent: *Nov. 1, 2005

(54) METHOD AND APPARATUS FOR REAL TIME MONITORING OF METALLIC CATION CONCENTRATIONS IN A SOLUTION

(75) Inventors: Herbert J. Kaiser, Pontoon Beach, IL (US); Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/896,609

(22) Filed: Jul. 21, 2004

(65) Prior Publication Data

US 2004/0263177 A1 Dec. 30, 2004

Related U.S. Application Data

(63) Continuation-in-part of application No. 10/389,036, filed on Mar. 14, 2003, now Pat. No. 6,844,742.

(51) Int. Cl.⁷ .......................... G01R 27/26; G01R 27/08

(52) U.S. Cl. ....................................... 324/663; 324/700

(58) Field of Search ................................ 324/700, 662, 324/658–691, 453; 148/252, 254

(56) References Cited

U.S. PATENT DOCUMENTS

| | | | |
|---|---|---|---|
| 3,636,444 A | 1/1972 | Strawn et al. | ................. 324/61 |
| 3,778,706 A | 12/1973 | Thompson | ................... 324/61 |
| 3,816,811 A | 6/1974 | Cmelik | ..................... 324/61 R |
| 4,031,742 A | 6/1977 | Michael et al. | .............. 73/40.7 |
| 4,158,810 A | 6/1979 | Leskovar | .................... 324/127 |

(Continued)

OTHER PUBLICATIONS

U.S. Appl. No. 10/456,378, filed Jun. 6, 2003, Centanni, entitled Method and Apparatus for Formulating and Controlling Chemical Concentrations in a Solution.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/872,227, filed Jun. 18, 2004, Kaiser et al., entitled: Method and Apparatus for Monitoring the Purity and/or Quality of Steam.

U.S. Appl. No. 10/900,745, filed Jul. 28, 2004, Kaiser et al., entitled: Method and Apparatus for Monitoring the state of a Chemical Solution for Decontamination of Chemical and Biological Warfare Agents.

U.S. Appl. No. 10/931,186,filed Aug. 31, 2004, Kaiser et al., entitled: Method and Apparatus for Monitoring Detergent Concentration in a Decontamination Process.

T. J. Buckley et al., "Torodial Cross Capacitor for Measuring the Dielectric Constant of Gases," Review of Scientific Instruments, vol. 71, No. 7, Jul. 2000, pp. 2914–2921.

Gross et al., "The Dielectric Constants of Water Hydrogen Peroxide and Hydrogen Peroxide–Water Mixtures," L. Amer. Chem. Soc., vol. 72, 1950, pp. 2075–2080, May 1950.

"Humidity Sensor Theory and Behavior," Psychometrics and Moisture, Honeywell HVAC, Nov. 27, 2002.

(Continued)

Primary Examiner—Anjan Deb
Assistant Examiner—Amy He
(74) Attorney, Agent, or Firm—Kusner & Jaffe; Michael A. Centanni (57) ABSTRACT

A method and apparatus for monitoring the concentration of metal cations in a chemical solution. In a preferred embodiment, the chemical solution is a solution for derouging or passivating stainless steel. A capacitive sensor provides data indicative of the concentration of chemical components (e.g., iron or chromium) in the chemical solution.

16 Claims, 3 Drawing Sheets

U.S. PATENT DOCUMENTS

| | | | |
|---|---|---|---|
| 4,219,776 A | 8/1980 | Arulanandan | 324/323 |
| 4,427,772 A | 1/1984 | Kodera et al. | 435/27 |
| 4,509,522 A | 4/1985 | Manuccia et al. | 128/634 |
| 4,525,265 A | 6/1985 | Abe et al. | 204/403 |
| 4,674,879 A | 6/1987 | Gregorig et al. | 356/301 |
| 4,769,593 A | 9/1988 | Reed et al. | 324/668 |
| 4,849,687 A | 7/1989 | Sims et al. | 324/668 |
| 4,857,152 A | 8/1989 | Armstrong et al. | 204/1 T |
| 5,151,660 A | 9/1992 | Powers et al. | 324/689 |
| 5,157,968 A | 10/1992 | Zfira | 73/149 |
| 5,171,523 A | 12/1992 | Williams | 422/20 |
| 5,179,926 A * | 1/1993 | Ament | 123/494 |
| 5,243,858 A | 9/1993 | Erskine et al. | 73/204.26 |
| 5,364,510 A | 11/1994 | Carpio | 204/153.1 |
| 5,439,569 A | 8/1995 | Carpio | 204/153.1 |
| 5,459,568 A | 10/1995 | Yano et al. | 356/336 |
| 5,470,754 A | 11/1995 | Rounbehler et al. | 436/106 |
| 5,600,142 A | 2/1997 | Van Den Berg et al. | 250/339.13 |
| 5,847,276 A | 12/1998 | Mimken et al. | 73/453 |
| 5,882,590 A | 3/1999 | Stewart et al. | 422/28 |
| 5,997,685 A | 12/1999 | Radhamohan et al. | 156/345 |
| 6,162,409 A | 12/2000 | Skelley et al. | 423/239.1 |
| 6,369,387 B1 | 4/2002 | Eckles | 250/343 |
| 6,454,874 B1 | 9/2002 | Jacobs et al. | 134/18 |
| 6,614,242 B2 | 9/2003 | Matter et al. | 324/698 |
| 6,660,231 B2 | 12/2003 | Moseley | 422/98 |
| 6,706,648 B2 | 3/2004 | Yamazaki et al. | 438/790 |
| 6,844,742 B2 * | 1/2005 | Centanni | 324/662 |
| 2002/0014410 A1 | 2/2002 | Silveri et al. | 204/412 |
| 2002/0033186 A1 | 3/2002 | Verhaverbeke et al. | 134/26 |
| 2002/0076492 A1 | 6/2002 | Loan et al. | 427/255.28 |
| 2002/0109511 A1 | 8/2002 | Frank | 324/663 |
| 2002/0111040 A1 | 8/2002 | Yamazaki et al. | 438/783 |
| 2002/0157686 A1 | 10/2002 | Kenny et al. | 134/1.3 |
| 2003/0063997 A1 | 4/2003 | Fryer et al. | 422/3 |
| 2003/0102007 A1 | 6/2003 | Kaiser | 134/1 |
| 2003/0157587 A1 | 8/2003 | Gomez et al. | 435/30 |
| 2004/0029257 A1 | 2/2004 | Dutil et al. | 435/266 |
| 2004/0079395 A1 | 4/2004 | Kim et al. | 134/30 |
| 2004/0178799 A1 | 9/2004 | Korenev et al. | 324/453 |
| 2004/0178802 A1 | 9/2004 | Centanni | 324/662 |
| 2004/0178803 A1 | 9/2004 | Centanni | 324/662 |
| 2004/0178804 A1 | 9/2004 | Allen et al. | 324/662 |
| 2004/0262170 A1 | 12/2004 | Centanni | 205/782 |
| 2005/0016828 A1 * | 1/2005 | Bednarek et al. | 203/1 |

OTHER PUBLICATIONS

Philipp, "*Charge Transfer Sensing,*" 1997, month not available.

Wojslaw, "*Everything You Wanted to Know About. Digitally Programmable Potentiometers,*" Catalyst Semiconductor, Inc., Oct. 17, 2001, Publication No. 6009.

Kittel, "*Introduction to Solid State Physics,*" Fourth Edition, John Wiley & Sons, Inc., 1971, month not available.

Philipp, "*The Charge Transfer Sensor,*" Sensors Magazine, Oct. 1999.

* cited by examiner

FIG. 4

METHOD AND APPARATUS FOR REAL TIME MONITORING OF METALLIC CATION CONCENTRATIONS IN A SOLUTION

RELATED APPLICATIONS

The present invention is a Continuation-In-Part (CIP) of U.S. application Ser. No. 10/389,036, filed Mar. 14, 2003, now U.S. Pat. No. 6,844,742, entitled "Method and Apparatus for Measuring Chemical Concentration in a Fluid," which is incorporated herein by reference in its entirety.

FIELD OF THE INVENTION

The present invention relates generally to monitoring chemical concentrations, and more particularly to a method and apparatus for real time monitoring of metallic cation concentrations in a solution.

BACKGROUND OF THE INVENTION

Various grades of stainless steel are commonly used in the construction of equipment used in manufacturing applications. For example, in the pharmaceutical industry, stainless steel is used in equipment used for the manufacture of pharmaceuticals. This equipment includes, but is not limited to, process vessels, piping, water systems and ancillary equipment. The most common grade of stainless steel used in pharmaceutical manufacturing equipment is Type 316L stainless steel. In such applications, it is particularly important to avoid the introduction of contaminants into the manufacturing process.

Typically, a "passive layer" (e.g., an oxide) is applied to the surface of the stainless steel by a passivation process. "Passivation" includes the chemical treatment of stainless steel with a mild oxidant, such as a nitric acid solution, for the purpose of enhancing the spontaneous formation of a protective passive film. The passive layer is a thin, adherent film or layer formed on the surface of the stainless steel as a protective coating to protect the underlying surface from further chemical reaction, such as corrosion, electrodissolution, or dissolution.

During the normal life of the stainless steel equipment, the passive layer of the stainless steel is worn away, thereby allowing corrosion to occur on the surface of the stainless steel due to the presence of iron oxide. This type of corrosion is commonly referred to as "rouge," since it may appear as a reddish layer on the surface of the stainless steel. Rouge corrosion may be localized corrosion limited to only a portion of the stainless steel surface, or may be a general corrosion encompassing the whole stainless steel surface.

Rouge corrosion must be removed periodically from the surface of the stainless steel in order to prevent contamination of chemicals (e.g., pharmaceutical products or intermediate products) prepared in the stainless steel equipment. The corrosion also needs to be removed prior to passivation or repassivation of the stainless steel equipment.

"Derouging" is a process wherein contaminants (e.g., exogenous iron or iron compounds) are removed from the surface of stainless steel by means of a chemical dissolution. It should be appreciated that derouging is an ongoing maintenance issue for manufacturers (e.g., pharmaceutical companies) that operate stainless steel systems with high purity water running at elevated temperatures. This includes, but is not limited to, vapor compression stills, multi-effect stills, clean steam generators, steam piping systems, WFI (water for injection) and purified water systems operating above ambient temperatures.

A typical "derouging" process includes treating the equipment with an acid solution that removes the surface contamination, but will not significantly affect the stainless steel itself. The acid solution may include, but is not limited to, mineral acids (e.g., nitric acid or phosphoric acid), organic acids (e.g., citric acid), etc. These acids can be formulated products or neat solutions. The acid solution is recirculated or otherwise brought into contact with the "rouged" surface of the stainless steel.

The progress of a derouging process is typically monitored by taking samples of the acid solution contacted with the surface of the stainless steel, and analyzing the samples for iron content. When the iron level in the acid solution reaches a maximum, it is presumed that the majority of the rouge corrosion has been removed from the surface of the stainless steel. As additional acid is added to the acid solution, the increase in the iron level in the acid solution will slow as the amount of remaining rouge corrosion is reduced. The derouging process is considered complete when the amount of iron entering the acid solution has declined to a relatively small amount. Throughout a typical derouging process, samples of the acid solution are repeatedly taken to a laboratory and analyzed for iron content.

A repassivation process follows the derouging process. The repassivation process includes treating the stainless steel with a passivating solution to provide a chromium rich surface layer. The passivating solution may include, but is not limited to, mineral acids (e.g., nitric acid or phosphoric acid), organic acids (e.g., citric acid), etc. These acids can be formulated products or neat solutions.

The passivating solution is recirculated or otherwise brought into contact with the derouged surface of the stainless steel. The passivating solution selectively dissolves iron from the top layer of the stainless steel to make the iron less available at the surface to form iron oxides. The passivating process removes the iron, and increases the concentration of chromium at the surface of the stainless steel. Iron levels can be monitored throughout this process in the same manner as described above in connection with the derouging process. The iron levels in the solution can be correlated with the progress of the passivation process.

Prior art processes for monitoring iron and chromium levels for the above-described processes are time consuming, do not occur in real time, and do not facilitate automated processes.

The present invention addresses these and other drawbacks to provide a method and apparatus for monitoring the concentration of metallic cation concentrations in a solution.

SUMMARY OF THE INVENTION

In accordance with a preferred embodiment of the present invention, there is provided a system for monitoring the concentration of a chemical component in a chemical solution used for at least one of derouging and passivating of stainless steel, the system comprising: (a) a capacitor having first and second plates exposed to the solution, said solution being a dielectric therebetween; and (b) processing means for determining a change in an electrical property of the capacitor, said change in the electrical property varying according to the concentration of the chemical component in the solution, wherein said chemical component is introduced into the chemical solution from a stainless steel article exposed to said chemical solution.

In accordance with another aspect of the present invention, there is provided a method for monitoring the concentration of a chemical component in a chemical solution used for at least one of derouging and passivating of stainless steel, the method comprising the steps of: (a) exposing a capacitor, having first and second parallel plates, to the chemical solution, said solution comprising a dielectric therebetween; and (b) determining a change in an electrical property of the capacitor, said change in the electrical property varying according to the concentration of the chemical component in the solution, wherein said chemical component is introduced into the chemical solution from a stainless steel article exposed to said chemical solution.

An advantage of the present invention is the provision of a method and apparatus for monitoring the concentration of metallic cation concentrations in a solution that allows in situ measurements.

Another advantage of the present invention is the provision of a method and apparatus for monitoring the concentration of metallic cation concentrations in a solution that allows progress of derouging and passivation processes to be monitored in situ.

Another advantage of the present invention is the provision of a method and apparatus for monitoring the concentration of metallic cation concentrations in a solution that reduces the time required to monitor derouging and passivation processes.

Another advantage of the present invention is the provision of a method and apparatus for monitoring the concentration of metallic cation concentrations in a solution that improves safety by limiting exposure to highly acidic solutions during monitoring of derouging and passivation processes.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
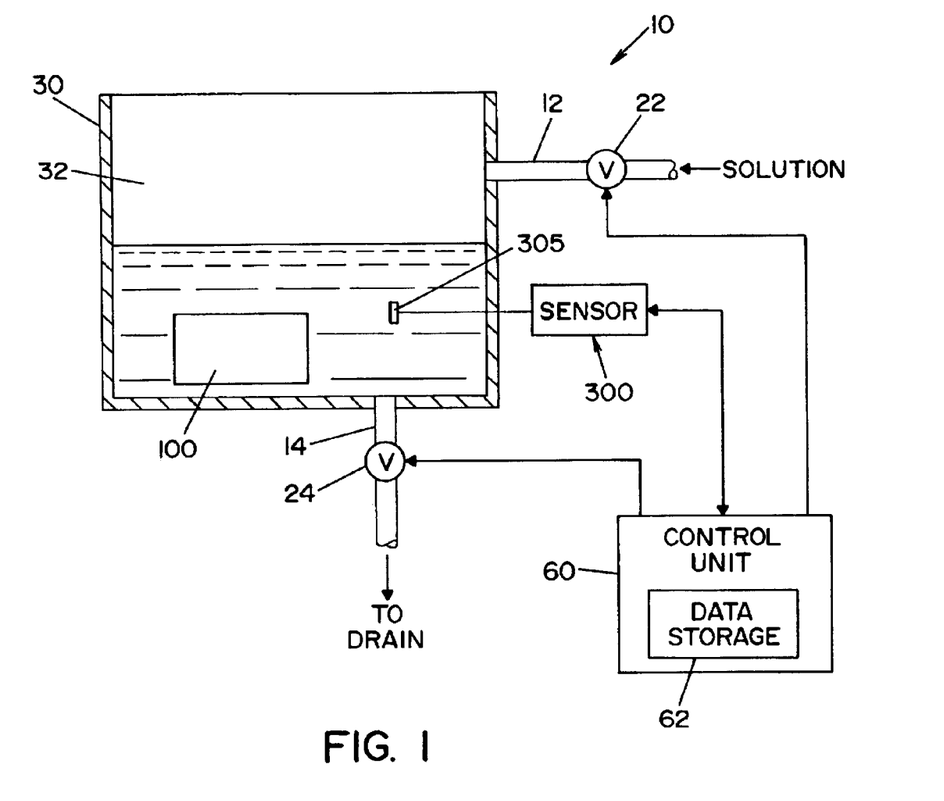
FIG. 1 is a cross-sectional side view of an apparatus for derouging and passivating stainless steel.

Referring now to the drawings wherein the showings are for the purpose of illustrating a preferred embodiment of the invention only, and not for the purpose of limiting same, FIG. 1 shows an apparatus 10 for derouging and passivating stainless steel. Apparatus 10 is basically comprised of a vessel 30, a control unit 60, and a sensor 300. Vessel 30 defines a chamber 32 dimensioned to receive a stainless steel article 100. By way of example, and not limitation, stainless steel article 100 may take of the form of a stainless steel component or stainless steel equipment. Articles 100 are placed into chamber 32 for exposure to chemical solutions for derouging and passivating.

Vessel 30 is fluidly connected with an input conduit 12 and an output conduit 14. A chemical solution (discussed below) flows into chamber 32 via input conduit 12. A valve 22 controls the flow of chemical solution into chamber 32. Output conduit 14 is in fluid communication with a drain. Valve 24 controls the flow of solution through output conduit 14.

Control unit 60 is a preferably a microprocessor or a microcontroller programmed to control operation of apparatus 10. In this regard, control unit 60 controls the operation of valves 22 and 24. Control unit 60 also preferably includes (or is connected with) a data storage device 62 for storing data.

Figure 2:
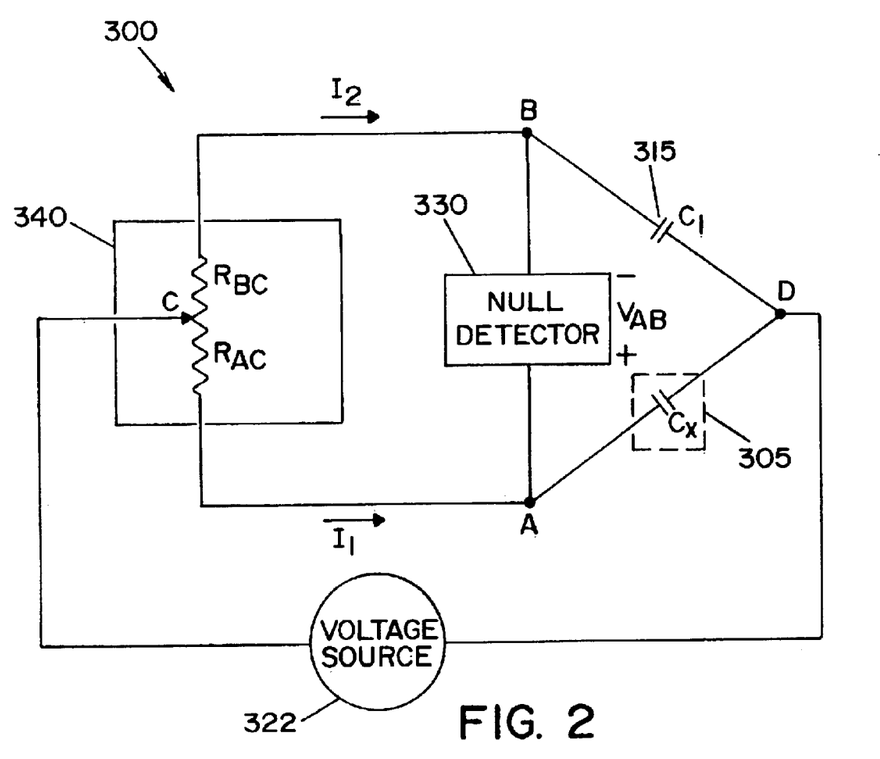
FIG. 2 is a schematic diagram of an exemplary capacitive sensor for monitoring metallic cation concentrations in a solution, according to a first embodiment.

Sensor 300 may take the form of any suitable sensing device responsive to changes in metallic cation concentrations. An exemplary sensor 300, is shown in FIG. 2. Sensor 300 is described in detail in U.S. patent application Ser. No. 10/389,036, filed Mar. 14, 2003, entitled "Method and Apparatus for Measuring Chemical Concentration in a Fluid," and U.S. patent application Ser. No. 10/405,880, filed Apr. 2, 2003, entitled "Method and Apparatus for Measuring Concentration of a Chemical Component in a Gas Mixture," which are fully incorporated herein in their entirety.

Sensor 300 is preferably disposed within chamber 32 to sense the concentration of metallic cation concentrations therein. However, it is contemplated that sensor 300 may alternatively be disposed within output conduit 14.

Sensor 300 includes a capacitor 305 that acts as a sensing element. Electrical properties of capacitor 305 are responsive to the concentration of chemical components in the chemical solution used in chamber 32. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

According to the embodiment illustrated in FIG. 2, sensor 300 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the concentration of chemical components used in chamber 32.

Sensor 300 is generally comprised of a voltage source 322, a null detector 330, an electronic potentiometer 340, a capacitor 315 of a known capacitance $C_1$, and capacitor 305 having a capacitance $C_x$.

Capacitor 305 is directly exposed to the chemical solution in chamber 32. The chemical solution fills the gap between the conducting plates of capacitor 305, thereby acting as the insulator or "dielectric" of capacitor 305. Capacitance $C_x$ of capacitor 305 will vary in accordance with the concentration of chemical components in the chemical solution.

It should be appreciated that the conducting plates of capacitor 305 should be isolated from the chemical solution to prevent damage to the conducting plates by the chemical components of the solution. For example, a polymeric tube may be used to isolate the chemical solution from the plates, wherein the conducting plates are located outside the tube, and the chemical solution flows through the tube. Alternatively, a polymer coating may be applied to the conducting plates.

In a preferred embodiment, capacitor 305 is a parallel plate capacitor. However, it should be appreciated that capacitor 305 could be constructed in a different form. For example, capacitor 305 could be a cylindrical or spherical capacitor. If a spherical capacitor is used as capacitor 305, holes must be placed in the outer shell of capacitor 305 such that the chemical solution can enter and exit the capacitor. The conducting plates may be made of copper.

Electronic potentiometer 340 functions in the same manner as a mechanical potentiometer. In this regard, electronic potentiometer 340 is a three terminal device. Between two of the terminals is a resistive element. The third terminal known as the "wiper" is connected to various points along the resistive element. In the illustrated embodiment, the wiper is digitally controlled by control unit 60 (see FIG. 1). The wiper divides the resistive element into two resistors $R_{BC}$ and $R_{AC}$. Electronic potentiometer 340 may take the form of a digitally programmable potentiometer (DPPTM) available from Catalyst Semiconductor, Inc. of Sunnyvale, Calif.

In a preferred embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described in detail. The elements of the bridge circuit are connected between junctions AC, BC, AD, and BD. Electronic potentiometer 340 is operated by control unit 60 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC} = V_{BC}, \text{ and } V_{AD} = V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC} = V_{BD}/V_{BC}$$

$$V_{AD} = V_{BD}/(V_{AC}/V_{BC})$$

Capacitor 305 of capacitance $C_x$ is connected between junctions A and D, and capacitor 315 of known capacitance $C_1$ is connected between junctions B and D. Electronic potentiometer 340, connected from junction A to junction C to junction B, is adjusted by control unit 60 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC} = I_1 R_{AC} \text{ and } V_{BC} = I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD} = V_{BD}/(V_{AC}/V_{BC})$, $V_{AC} = I_1 R_{AC}$, and $V_{BC} = I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

Differences in dipole moments of different molecules between the plates of capacitor 305 will affect the electrical properties (e.g., dielectric constant) of capacitor 305. Similarly, the presence of free charges between the plates of capacitor 305 will affect the electrical properties of capacitor 305. Changes to the electrical properties of capacitor 305 are used to monitor the concentration of chemical components in the chemical solution. As discussed above, chemical solution fills the gap between the conducting plates of capacitor 305, thereby acting as the dielectric of capacitor 305. By configuring capacitor 305 as an element of a bridge circuit, a measure of resistance values $R_{AC}$ and $R_{BC}$, when the bridge is balanced or nulled, can be used to determine the capacitance $C_x$ of capacitor 305. The capacitance $C_x$ of capacitor 305 is indicative of the concentration of the chemical components in the chemical solution, since the permittivity of the respective dielectric is affected by the relative concentration of the chemical components in the chemical solution.

It is well known that for a parallel plate capacitor $C = (k \in_0)(A/d) = (\in)(A/d)$, where C is capacitance, k is the dielectric constant, $\in_0$ is the permittivity of free space ($8.85 \times 10^{-12}$ F/m), $\in$ is the permittivity (Farads/meter) of the capacitor dielectric, A is the area of the capacitor plates (m$^2$), and d is the separation in meters between the capacitor plates. As $\in$ increases, the capacitance C will increase. Where the capacitor is a parallel plate capacitor with circular plates of diameter D, $C = (\pi D^2 \in)/(4d)$.

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi fC)$). Accordingly, frequency of the waveform generated by voltage source 322 influences the response of capacitors. Thus, the frequency selected for voltage source 322 should preferably be a frequency that will provide a generally linear response for capacitance as the concentration of chemical components of the chemical solution is varied. This will facilitate the use of interpolation and extrapolation of capacitance values, as will be discussed further below. If a suitable linear response is not obtained, then an expanded set of data points should be stored in data storage device 62.

Figure 3:
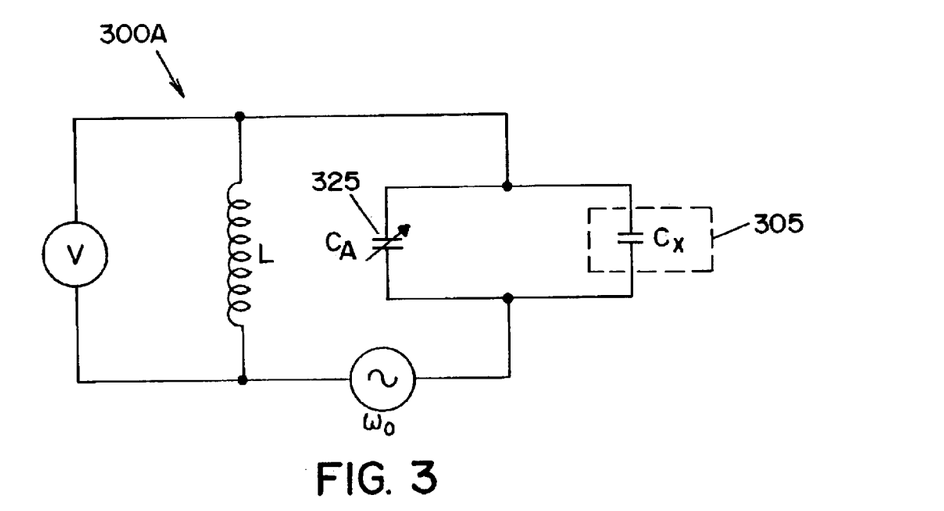
FIG. 3 is a schematic diagram illustrating an exemplary capacitive sensor for monitoring metallic cation concentrations in a solution, according to a second embodiment.

It should be appreciated that while a preferred embodiment of the present invention includes a sensor 300 in the form of a bridge circuit, other types of circuits and techniques (including other types of bridge circuits, and capacitance meters) known to those skilled in the art, may be suitably used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0=[L(C_A+C_x)]^{-1/2}$, the unknown capacitance $C_x$ of capacitor 305 can be determined.

Figure 4:
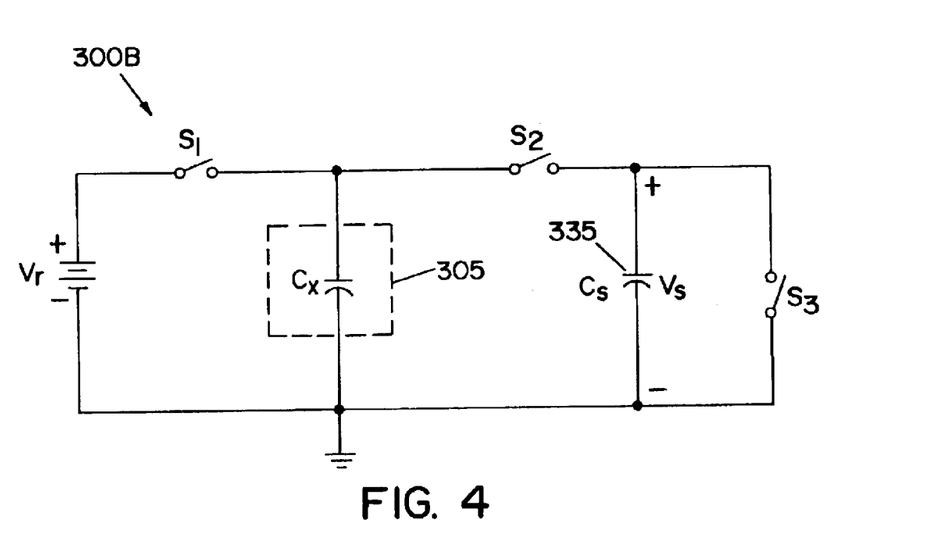
FIG. 4 is a schematic diagram illustrating an exemplary capacitive sensor for monitoring metallic cation concentrations in a solution, according to a third embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$ of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, chemical solution in chamber 32 fills the gap between the conducting plates of capacitor 305, thereby acting as an insulator or "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 335 is selected to be significantly larger than capacitor 305.

The equations governing sensor 300B are as follows:

$V_s=V_r[C_y/(C_y+C_s)]$, therefore $C_y=V_sC_s/[V_r-V_s]$.

The charge-transfer sensor has been applied in a self-contained capacitance-to-digital-converter (CDC) integrated circuit (IC). For example, Quantum Research Group produces a QProx™ CDC sensor IC (e.g., QT 300 and QT 301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10–7 pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

Referring now to FIG. 2, monitoring of iron concentration in the chemical solution in chamber 32 will now be described in connection with sensor 300. However, it should be appreciated that other metallic cations in the chemical solution may be monitored, including, but not limited to chromium.

Capacitor 305 is exposed to known concentrations of iron in (1) a chemical solution for derouging stainless steel and (2) a chemical solution for passivation of stainless steel to develop a set of data, or a curve, of capacitance values $C_x$ as a function of concentration of iron in each chemical solution. For example, capacitance values $C_x$ may be determined for iron concentrations ranging from 0% to 90% (at increments of 2% to 5%). The associated set of data, or curve, is programmed or stored in data storage device 62 of control unit 60. As the concentration of the iron is varied in each of the chemical solutions, the corresponding capacitance $C_x$ of capacitor 305 is determined, and stored in data storage device 62.

After the set of data is stored in data storage device 62 for the derouging chemical solution and the passivation chemical solution, monitoring of the concentration of iron in the derouging and passivation chemical solutions can commence. Capacitor 305 is exposed to a chemical solution. A determination of $R_{AC}$ and $R_{BC}$ when the bridge is nulled is then used to determine a value for the capacitance $C_x$ of capacitor 305. As discussed above, $C_x=C_1 (R_{BC}/R_{AC})$. The data stored in data storage device 62 is searched for the measured capacitance value $C_x$ to obtain the corresponding concentration of iron.

A linear relationship between concentration and capacitance allows one to normalize any measurement made so as to provide the absolute concentration of the iron. If the measured capacitance $C_x$ of capacitor 305 is not found in the pre-stored data, the stored data may be interpolated or extrapolated to obtain a concentration corresponding to the measure capacitance $C_x$ of capacitor 305. As noted above, frequency of the waveform generated by voltage source 322 will influence the response of capacitors. Where the capacitance $C_x$ of capacitor 305 does not exhibit a suitable linear response, an expanded set of data points should be stored in data storage device 62, so that interpolation or extrapolation is unnecessary.

It should be appreciated that while a preferred embodiment of the present invention uses a measure of a capacitor's capacitance to monitor concentration, it is also contemplated that a measure of other electrical properties associated with a capacitor may be used to monitor concentration, including, but not limited to, the permittivity and dielectric constant of the capacitor dielectric.

The present invention shall now be further described with reference to the operation of apparatus 10 (FIG. 1). A stainless steel article 100 is placed in chamber 32 of vessel 30. Control unit 60 opens valve 22 to allow a chemical solution to fill chamber 32. The first chemical solution to fill chamber 32 is a chemical solution suitable for derouging stainless steel. The second chemical solution to fill chamber 32 is a chemical solution suitable for passivating stainless steel.

Parameters for some typical chemical solutions used in derouging and passivating Type 316L stainless steel are provided in the tables set forth below. It should be appreciated that the chemical solution parameters (i.e., time of exposure, temperature and concentration) will be a function of the type of alloy processed.

| Nitric Acid Chemical Solution Parameters | |
|---|---|
| Nitric Acid | 20% to 50% (by volume) |
| Water | 50% to 80% (by volume) |
| Temperature | 60° F. to 160° F. |
| Exposure Time | 20 minutes to 120 minutes |

| Citric Acid Chemical Solution Parameters | |
|---|---|
| Citric Acid | 4% to 10% (by weight) |
| Water | 90% to 96% (by weight) |
| Temperature | 150° F. to 170° F. |
| Exposure Time | 30 minutes to 10 hours |

The chemical solutions for derouging and passivating stainless steel may also include additional chemical components, including, but not limited to, sodium dichromate, or EDTA (ethylenediaminetetraacetic acid). Details on chemical solution for derouging and passivating can be found in ASTM A380 and ASTM A967.

In a derouging process, contaminants (e.g., exogenous iron or iron compounds) are removed from the surface of stainless steel by means of a chemical dissolution. Sensor 300 monitors the concentration of iron in the chemical solution in chamber 32 to monitor the progress of the derouging process. In this regard, the derouging process is determined to be complete when the increase in the iron concentration in the chemical solution is relatively small.

When sensor 300 has detected that the concentration of iron in chamber 32 is indicative of a completed derouging process, valve 24 is opened by sensor 300 to drain the chemical solution from chamber 32. Chamber 32 may then be rinsed with a cleaning solution (e.g., water) to remove any residual chemical solution. Thereafter, chamber 32 may be filled with a chemical solution for passivating the stainless steel.

In a passivating process, a chromium rich surface layer is formed on the stainless steel by means of a chemical solution. In this regard, a chemical solution selectively dissolves iron from the top layer of the stainless steel to make the iron less available at the surface to form iron oxides. The concentration of iron dissolved in the chemical solution can be correlated with the progress of the passivation process. For instance, a correlation may be established between a measured iron concentration and an amount of iron removed from the surface of the stainless steel. When sensor 300 has detected that the concentration of iron in chamber 32 is indicative of a completed passivating process (e.g., removal of iron to a depth of about 50 Å), valve 24 may again be opened to drain the chemical solution from chamber 32. Chamber 32 may then be rinsed with a cleaning solution (e.g., water) to remove any residual chemical solution.

It should be appreciated that sensor 300 may also be used to detect when a maximum concentration of iron has been reached in the chemical solution in chamber 32. In this regard, a maximum concentration of iron may be detected when no further change to the measured capacitance $C_x$ is detected during a derouging or passivating process.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for monitoring the concentration of a chemical component in a chemical solution used for at least one of derouging and passivating of stainless steel, the system comprising:
    a capacitor having first and second conducting elements exposed to the solution, said solution being a dielectric therebetween; and
    processing means for determining a change in an electrical property of the capacitor, said change in the electrical property varying according to the concentration of the chemical component in the solution, wherein said chemical component is introduced into the chemical solution from a stainless steel article exposed to said chemical solution.

2. A system according to claim 1, wherein said chemical component is a metal cation.

3. A system according to claim 2, wherein said metal cation is iron.

4. A system according to claim 2, wherein said metal cation is chromium.

5. A system according to claim 1, wherein said processing means includes a memory for storing a set of data including values of the electrical property and corresponding concentration values indicative of the concentration of the chemical component in the chemical solution.

6. A system according to claim 1, wherein said solution includes at least one of: a mineral acid and an organic acid.

7. A system according to claim 6, wherein said mineral acid is selected from the group consisting of: nitric acid and phosphoric acid.

8. A system according to claim 6, wherein said organic acid is citric acid.

9. A method for monitoring the concentration of a chemical component in a chemical solution used for at least one of derouging and passivating of stainless steel, the method comprising:
    exposing a capacitor, having first and second conducting elements, to the chemical solution, said solution comprising a dielectric therebetween; and
    determining a change in an electrical property of the capacitor, said change in the electrical property varying according to the concentration of the chemical component in the solution, wherein said chemical component is introduced into the chemical solution from a stainless steel article exposed to said chemical solution.

10. A method according to claim 9, wherein said step of determining the change in an electrical property of the capacitor includes:

accessing pre-stored data including values of the electrical property and corresponding concentration values indicative of the concentration of the chemical component in the solution.

11. A method according to claim 9, wherein said chemical component is a metal cation.

12. A method according to claim 11, wherein said metal cation is iron.

13. A method according to claim 11, wherein said metal cation is chromium.

14. A method according to claim 9, wherein said solution includes at least one of: a mineral acid and an organic acid.

15. A method according to claim 14, wherein said mineral acid is selected from the group consisting of: nitric acid and phosphoric acid.

16. A method according to claim 14, wherein said organic acid is citric acid.

* * * * *